United States Patent [19]

Mueller et al.

[11] Patent Number: 4,508,924
[45] Date of Patent: Apr. 2, 1985

[54] PREPARATION OF O-ACYLPHENOLS AND P-ACYLPHENOLS

[75] Inventors: Josef Mueller, Ludwigshafen; Walter-Wielant Wiersdorff, Mutterstadt; Werner Kirschenlohr, Ludwigshafen; Gerd Schwantje, Wachenheim, all of Fed. Rep. of Germany

[73] Assignee: BASF Aktiengesellschaft, Fed. Rep. of Germany

[21] Appl. No.: 548,215

[22] Filed: Nov. 1, 1983

Related U.S. Application Data

[63] Continuation of Ser. No. 344,014, Jan. 29, 1982, abandoned.

[30] Foreign Application Priority Data

Mar. 4, 1981 [DE] Fed. Rep. of Germany ....... 3108076

[51] Int. Cl.$^3$ .............................................. C07C 45/46
[52] U.S. Cl. .................................................. 568/322
[58] Field of Search ................ 568/322, 323, 364, 407

[56] References Cited

U.S. PATENT DOCUMENTS

| | | | |
|---|---|---|---|
| 2,189,383 | 2/1940 | Ralston et al. | 568/323 |
| 2,212,478 | 8/1940 | Miller | 568/323 |
| 3,146,269 | 8/1964 | Braus et al. | 568/322 |
| 3,548,005 | 12/1970 | Milionis et al. | 568/322 |
| 3,769,349 | 10/1973 | Yukutomi et al. | 568/322 |
| 3,843,729 | 10/1974 | Lochmann et al. | 568/322 |
| 3,907,837 | 9/1975 | Effenberger et al. | 568/323 |
| 4,268,691 | 5/1981 | Fung et al. | 568/322 |
| 4,326,083 | 4/1982 | McKellin | 568/322 |

Primary Examiner—James H. Reamer
Attorney, Agent, or Firm—Keil & Weinkauf

[57] ABSTRACT o-Acylphenols and p-acylphenols are prepared by reacting phenol with an acid halide and aluminum chloride, using a halobenzene as the solvent, at from 15° to 55° C. and then at from 55° and 200° C.

The compounds obtainable by the process of the invention are valuable starting materials for the preparation of drugs, pesticides and dyes.

9 Claims, No Drawings

PREPARATION OF O-ACYLPHENOLS AND P-ACYLPHENOLS

This is a continuation of application Ser. No. 344,014, filed Jan. 29, 1982 now abandoned.

The invention relates to a novel process for the preparation of o-acylphenols and p-acylphenols by reacting phenol with an acid halide and aluminum chloride, using a halobenzene as the solvent, at from 15° to 55° C. and then at from 55° to 200° C.

It is known that chlorobenzene can be acylated, even at room temperature, using $AlCl_3$ as the catalyst (Ber. 42 (1909), 1812; Bull. Soc. Chem. Belg. 61 (1952), 694–696).

Furthermore, it is known that a mixture of o-acylphenols and p-acylphenols is formed in the Fries rearrangement, the proportion of the p-product is general strongly predominating. Frequently used solvents are $CS_2$, $CH_2Cl\text{—}CH_2\text{—}Cl$ and nitrobenzene. Although the o-selectivity can be increased by carrying out the reaction in the absence of a solvent, this procedure is very difficult to put into practice industrially since, at high conversions, very viscous, scarcely stirrable masses are formed, the hydrolysis of which presents difficulties (Ann. 460 (1928), 56–98).

In addition, under the reaction conditions described, the o-acylphenols can only be isolated by steam distillation, while the p-products can only be obtained in pure form by repeated recrystallization.

Furthermore, high selectivities of o-compounds are supposed to have been achieved using gasolines as solvents (Tetrahedron 20 (1964), 1661–1666).

However, two-phase highly viscous masses which are no longer stirrable are also formed under these reaction conditions.

We have found that o-acylphenols and p-acylphenols of the formula

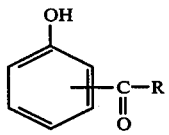

I where the acyl radical is in the o-position and/or p-position to the hydroxyl group, and R is an aliphatic, cycloaliphatic or araliphatic radical, are advantageously obtained if phenol is reacted with an acid halide of the formula

II where R has the above meanings and X is halogen, in an amount of from 0.5 to 1.5 moles per mole of phenol, in the presence of from 0.5 to 1.5 moles of aluminum chloride per mole of phenol, and of a halobenzene as the solvent, initially at from 15° to 55° C. and then at from 55° to 200° C.

If propionyl chloride is used, the reaction can be represented by the following equation:

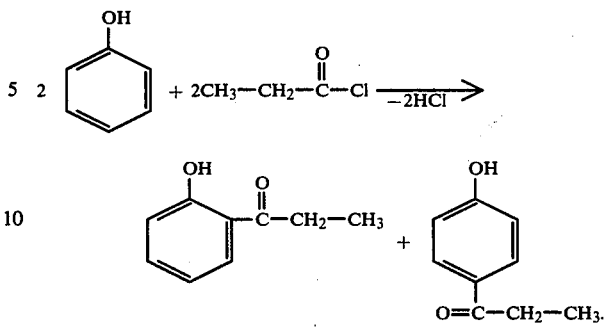

Compared to the known processes, the process according to the invention gives o-acylphenols and p-acylphenols by a simpler and more economical route and in better yield, purity and space/time yield. The p-products I crystallize out in high purities, after the addition of ice water, while the o-derivatives remaining in the mother liquor are obtained in good purity by simple distillation. There are no difficulties in handling (stirring) the reaction mixture. All these advantageous results are surprising in the light of the prior art. It was not to be expected that the measures according to the invention would not lead, to a significant degree, to acylation of halobenzenes, the formation of corresponding halogenated by-products or increased amounts of esters.

The starting material II is reacted with phenol in a stoichiometric amount or in an excess of either component, namely in a ratio of from 0.5 to 1.5 moles, preferably from 0.95 to 1.1 moles, of starting material II per mole of phenol. Preferred starting materials II, and accordingly preferred end products I, are those in whose formulae the acyl radical is in the o-position and/or p-position to the hydroxyl group, $R^1$ is alkyl of 1 to 6 carbon atoms, cycloalkyl of 5 to 8 carbon atoms or aralkyl of 7 to 12 carbon atoms, and X is bromine or, in particular, chlorine. The above radicals can additionally be substituted by groups which are inert under the reaction conditions, for example alkyl or alkoxy of 1 to 4 carbon atoms each.

Examples of suitable starting materials II are acetyl chloride, propionyl chloride, butyryl chloride, isobutyryl chloride, valeryl chloride, isovaleryl chloride, caproyl chloride, heptanoyl chloride and caprylyl chloride, and the corresponding bromides.

The reaction is carried out in the presence of from 0.5 to 2, advantageously from 0.95 to 1.1, mole of aluminum chloride per mole of phenol. Monobromobenzenes, monochlorobenzenes, dibromobenzenes and dichlorobenzenes are preferred solvents. From 100 to 10,000 advantageously from 130 to 200, percent by weight of solvent based on phenol, is used. The reaction is carried out in 2 temperature ranges, initially at from 15° to 55° C., advantageously from 40° to 51° C., and then at from 55° to 200° C., advantageously from 80° to 130° C., under atmospheric or superatmospheric pressure, and continuously or batchwise.

The reaction can be carried out in the following manner: a mixture of phenol, the acid chloride, the halobenzene and aluminum chloride is kept for from 0.2 to 1 hour at the reaction temperature of the 1st stage and then for from 0.5 to 3 hours at the reaction temperature of the 2nd stage. The end product I is then isolated in a conventional manner, for example by adding ice water, filtering off the p-product I, fractionally distilling the filtrate and isolating the o-component I.

The compounds obtainable by the process according to the invention are valuable starting materials for the preparation of drugs, pesticides and dyes. Regarding the use of these compounds, reference may be made to the above literature.

In the Examples which follow, parts are by weight.

EXAMPLE 1 o-Hydroxypropiophenone and p-hydroxypropiophenone 1,350 parts of AlCl$_3$ are metered into a mixture of 940 parts of phenol in 1,500 parts of chlorobenzene at a rate such that 40° C. is not exceeded. 1,017 parts of propionyl chloride are then added in the course of 60 minutes at a rate such that 50° C. is not exceeded. Thereafter the mixture is heated to 105° C., and stirring is continued at this temperature for 2 hours. 10,000 parts of ice water are added and the precipitated p-product I is filtered off. The phases are separated, the chlorobenzene is stripped off under reduced pressure and the o-product I is distilled at from 125° to 133° C., under 30 mbar.

Yield: o-hydroxypropiophenone: 1,083 parts (68% of theory), boiling point: 115°–117° C./20 mbar, p-hydroxypropiophenone: 330 parts (22% of theory), Melting point: 148° C.

EXAMPLES 2 AND 3

The following compounds are prepared similarly to Example 1:

o-hydroxyacetophenone: 830 parts (61% of theory), boiling point 115°–119° C./30 mbar, p-hydroxyacetophenone: 381 parts (28% of theory), melting point: 104°–105° C.

EXAMPLE 4

534 parts of AlCl$_3$ are metered into a mixture of 188 parts of phenol in 600 parts of o-dichlorobenzene at a rate such that 40° C. is not exceeded. 185 parts of propionyl chloride are then added in the course of 60 minutes at a rate such that 50° C. is not exceeded. Thereafter the mixture is heated to 105° C. in the course of one hour, and stirring is continued for another 15 minutes. 2,500 parts of ice water are added and the precipitated p-product I is filtered off. The solid is rinsed with toluene and dried. The combined organic phases are distilled.

Yield: p-hydroxyprophenone: 236 parts (79% of theory), melting point: 148° C., o-hydroxypropiophenone: 55 parts (18% of theory), boiling point: 115°–118° C./20 mbar.

EXAMPLE 5 (COMPARATIVE EXAMPLE)

133.5 parts of AlCl$_3$ are added a little at a time to 136 parts of phenyl acetate, and the mixture is then heated to 170° C. for one hour. This results in a highly viscous, dark mass which can no longer be stirred and which, after cooling, is decomposed with 1,000 parts of ice water. The mixture is subjected to steam distillation. Subsequent purification by distillation gives 36 parts (26.4% of theory) of o-hydroxyacetophenone. It is not possible to isolate the p-product in pure form. When the experiment is repeated several times, yields of o-hydroxyacetophenone of from 22 to 30% are obtained.

EXAMPLE 6 (COMPARATIVE EXAMPLE)

133.5 parts of aluminum chloride are suspended in 300 parts of n-heptane, and 94 parts of phenol are added to the suspension. 78.5 parts of acetyl chloride are added slowly, at 22° C., whilst stirring, and the mixture is then refluxed. As soon as a conversion of 30% of theory is reached, the reaction has to be stopped because the mixture is too viscous to stir.

EXAMPLE 7 (COMPARATIVE EXAMPLE)

A mixture of 133.5 parts of AlCl$_3$ and 300 parts of chlorobenzene is heated to 100° C., and 136 parts of phenyl acetate are added at a rate such that 110° C. is not exceeded (namely, in 0.5 hour). After the addition, stirring is continued at this temperature for another hour and the mixture is then hydrolyzed by pouring it onto 1,000 parts of ice water. 33 parts (24% of theory) of p-hydroxyacetophenone are isolated. After distillation of the mother liquor, a total of 87 parts of reaction mixture, of the following overall yield, is obtained (gas chromatographic determination):

| | |
|---|---|
| phenol | (18.4% of theory) |
| o-hydroxyacetophenone | (34% of theory) |
| p-hydroxyacetophenone | (24% of theory) |
| p-chloroacetophenone | (22.6% of theory) |
| other by-products | (1% of theory). |

We claim:
1. A process for the preparation of o-acylphenols and p-acylphenols of the formula

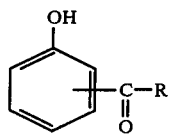

where the acyl radical is in the o-position and/or p-position to the hydroxyl group, and R is an aliphatic or cycloaliphatic radical, wherein phenol is reacted with an acid halide of the formula

where R has the above meanings and X is halogen, in an amount of from 0.5 to 1.5 moles permole of phenol, in the presence of from 0.5 to 1.5 moles of aluminum chloride per mole of phenol, and of a halobenzene as the solvent, initially at from 15° to 55° C. and then at from 55° to 200° C.

2. The process of claim 1, wherein the reaction is carried out using from 0.95 to 1.1 mole of starting material II per mole of phenol.

3. The process of claim 1, wherein the reaction is carried out using from 100 to 10,000 percent by weight of solvent, based on phenol.

4. The process of claim 1, wherein the first stage of the reaction is carried out at from 40° to 51° C.

5. The process of claim 1, wherein the second stage of the reaction is carried out at from 56° to 200° C.

6. The process of claim 1, wherein the second stage of the reaction is carried out at from 80° to 130° C.

7. The process of claim 4, wherein the second stage of the reaction is carried out at from 80° to 130° C.

8. The process of claim 1, wherein R is alkyl of 1 to 6 carbon atoms and wherein X is chlorine.

9. The process of claim 1, wherein R is cycloalkyl of 5 to 8 carbon atoms and wherein X is chlorine.

* * * * *

UNITED STATES PATENT AND TRADEMARK OFFICE
CERTIFICATE OF CORRECTION

PATENT NO. : 4,508,924
DATED : April 2, 1985
INVENTOR(S) : Josef MUELLER et al.

It is certified that error appears in the above-identified patent and that said Letters Patent is hereby corrected as shown below:

<u>IN THE ABSTRACT</u>:

Line 4, should read "to 200°C" rather than "and 200°C".

Claim 1 line 11, should read "2.0 moles" rather than "1.5 moles".

Signed and Sealed this

Twenty-third Day of July 1985

[SEAL]

Attest:

DONALD J. QUIGG

*Attesting Officer*     *Acting Commissioner of Patents and Trademarks*